(12) United States Patent
Djurovic

(10) Patent No.: US 6,221,085 B1
(45) Date of Patent: *Apr. 24, 2001

(54) DJUROVIC SUTURING DEVICE

(76) Inventor: Zarija Djurovic, 370 Devon Ct., Valparaiso, IN (US) 46383

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/233,664

(22) Filed: Jan. 18, 1999

(51) Int. Cl.[7] .................................................. H01B 17/04
(52) U.S. Cl. ........................................... 606/148; 606/144
(58) Field of Search ........................... 606/148, 139–144, 606/212

(56) References Cited

U.S. PATENT DOCUMENTS

| | | | |
|---|---|---|---|
| Re. 14,923 | * | 7/1920 | Smit ...................................... 606/144 |
| 67,545 | * | 8/1967 | Hodgins . |
| 2,737,954 | * | 2/1954 | Knapp . |
| 3,638,654 | * | 2/1972 | Akuba .................................. 606/144 |
| 4,011,873 | * | 3/1977 | Hoffmeister . |
| 4,484,580 | * | 11/1984 | Notomo et al. ...................... 606/144 |
| 5,207,693 | * | 5/1993 | Phillips . |
| 5,350,385 | * | 9/1994 | Christy . |
| 5,356,424 | * | 10/1994 | Buzerak et al. . |
| 5,431,666 | * | 7/1995 | Sauer et al. . |
| 5,437,266 | * | 8/1995 | McPherson et al. . |
| 5,653,716 | * | 8/1997 | Malo et al. . |
| 5,709,692 | * | 1/1998 | Mollenauer et al. . |
| 5,776,148 | * | 7/1998 | Christy . |

* cited by examiner

Primary Examiner—Michael Buiz
Assistant Examiner—Anthony King

(57) ABSTRACT

A suturing device consists of a needle and a turning mechanism that drives the needle. A handle of the device drives the turning mechanism. The device receives suturing material needed for suturing tissue; and a surgeon may operate it by squeezing the handle. This action may move the needle from zero to 360 degrees.

9 Claims, 3 Drawing Sheets

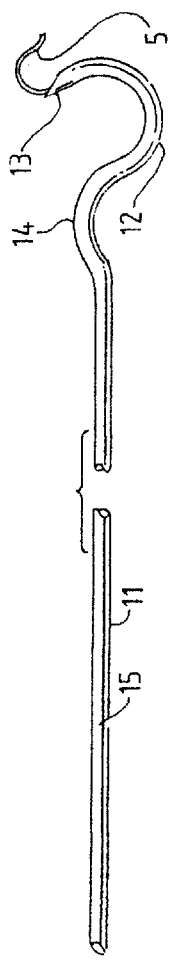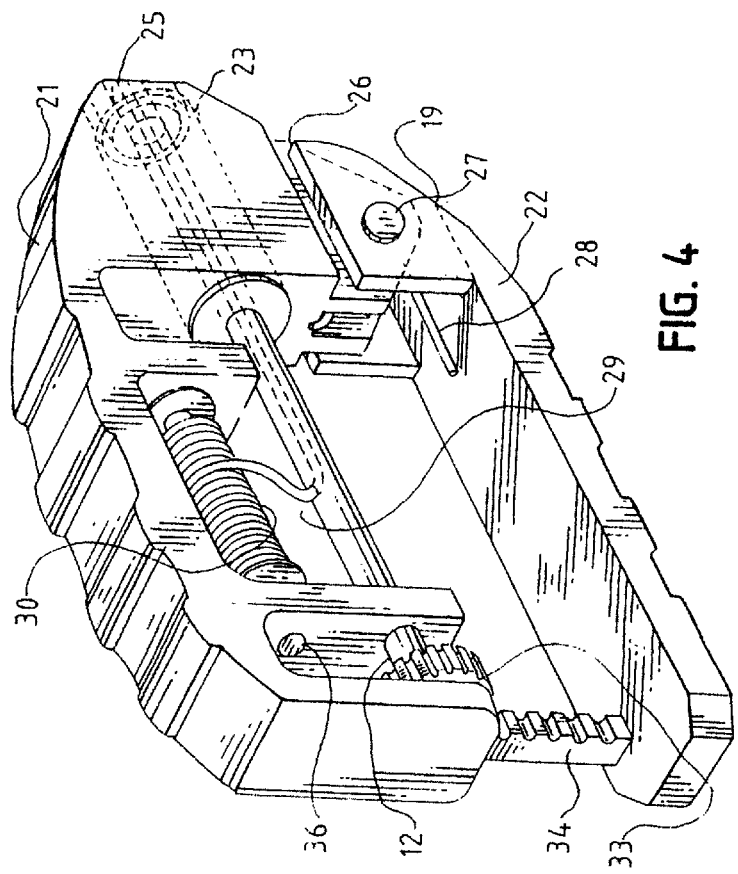
FIG. 2
FIG. 3
FIG. 4

DJUROVIC SUTURING DEVICE

BACKGROUND OF THE INVENTION

1. Field of the Invention

The present invention relates to a laparoscopic surgical device that allows a surgeon to safely and with much greater control place the stitch on the tissue that needs to be sutured. Suturing in laparoscopic surgery at the present time is one of the most difficult parts of the procedure.

2. Description of the Prior Art

At the present time, laparoscopic surgeons are using a standard needle with suture material that is grasped with the needle holder, and is passed through the surgical port in the patient's abdomen. Once the needle is passed through the tissue that needs to be sutured, the surgeon must release the needle holder, grab the tip of the needle, and pull it out of the tissue. It is very difficult for surgeons to again grab the needle in the proper position to be able to make the next stitch. This process requires, in many cases, multiple attempts to pass the stitch, which increases the time and cost of the surgical procedures. With the Suturing Device of the present invention the surgeon will have much greater control placing the stitch, which will be more convenient for both the surgeon and the patient.

SUMMARY OF THE INVENTION

The suturing device of the present invention is designed in such a way that a surgeon's hand is in full control of the needle and the suture material where he does not need to grab or release the needle but actually just grab the suture material that comes out of the needle hole. With this instrument, the surgeon is able to place a single stitch or suture in the tissue in a continued stitching manner.

The spool is capable of holding a load of suture material in different lengths that satisfy shorter or longer procedures, and is separately prepared and sterilized for surgical procedures. A single squeeze of the handle by the surgeon activates the moving mechanism and turns the needle up to 360 degrees, which is normally more than enough to get through the tissue that needs to be sutured.

The present invention includes a proximal end and a distal end where the proximal end is a handle made of two portions, one being stationary and the other moving.

The moving portion turns the gear placed in the proximal end of the stationary portion which is connected with the proximal end of the needle. The gear is turned by squeezing the moving portion of the handle, which will actually turn the needle up to 360 degrees.

The distal end is a semi-circular tubular needle with a sharp cutting tip and an opening for the passage of suture material. This opening is placed in an oblique shape that is on the outside of the semi-circular needle, through which the surgeon can grab the suture material much easier than if the opening is facing the inside of the semi-circular needle.

The transitional portion of the needle is the portion in between the semi-circular portion and the proximal portion of the needle, which lays in the axial center of the semi-circular needle. The proximal end of the needle passes through the distal bushing of the distal tubular shaft of the instrument which is placed in between the distal bushing and the proximal bushing that is in the stationary portion of the handle. This tubular portion is made of different diameters such as 5, 10, 12 mm outside diameter, or any other desired diameter that fits in the existing cannulus used in the laparoscopic surgery.

The proximal end of the needle extends to the turning shaft placed in the stationary portion of the handle through the proximal bushing with its distal ends and the proximal end is secured in the very proximal portion of the stationary portion of the handle.

The proximal end of the needle finishes in the top opening of the turning shaft for the placement of suture material.

Suture material is stored on a removable and disposable spool which is placed in the middle portion of the stationary portion of the handle.

The joint of the moving and stationary portions of the handle has a spring that will automatically return the moving part of the handle in its original position, and also return the needle to its original position. In this way, the surgeon will need to concentrate only on the site of the needle penetration.

These and other objects, aspects, features, and advantages of the present invention will become apparent from the following detailed description of the preferred embodiment taken in conjunction with the accompanying drawings.

BRIEF DESCRIPTION OF THE DRAWINGS

For a more complex understanding of this invention, one should now refer to the embodiment illustrated in greater detail in the accompanying drawings and described below by way of an example of the invention. In the drawings:

FIG. 2 is a side view of the distal end of the present invention representing the semi-circular needle;

FIG. 3 is a sectional view of the tubular portion of the present invention that connects the distal bushing with the stationary portion of the handle;

FIG. 4 is a perspective view of the handle of the present invention, displaying both the stationary and the moving portions of the handle;

While the following disclosure describes the invention in connection with one embodiment, one should understand that the invention is not limited to this embodiment. Furthermore, one should understand that the drawings are not to scale and that graphic symbols, diagrammatic representatives, and fragmentary views, in part, illustrate the embodiment. In certain instances, the disclosure may not include details which are not necessary for an understanding of the present invention such as conventional details of fabrication and assembly.

DESCRIPTION OF THE DRAWINGS

For ease of reference, as used herein the term "distal" will refer to that part of the instrument which is farthest for the surgeon, and the term "proximal" refers to that part of the suturing device which is closest to the surgeon.

Figure 1:
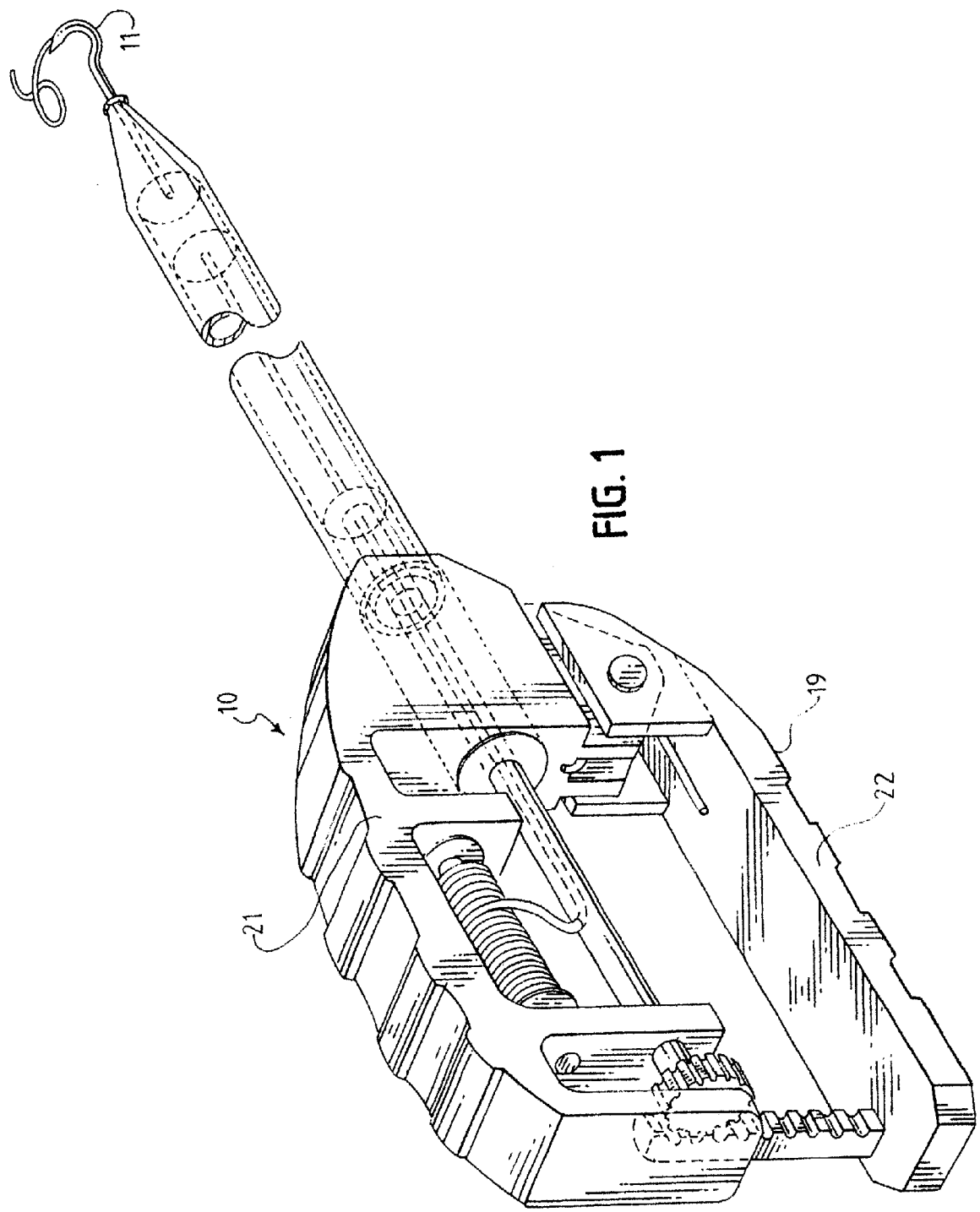
FIG. 1 is a perspective view of the Suturing Device of the present invention with a portion cut away to show the internal contents.
Figure 5:
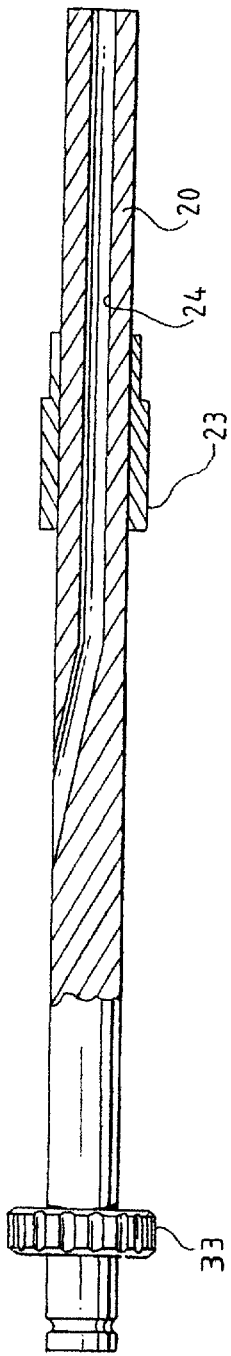
FIG. 5 is a partial sectional view of the turning shaft including the turning gear of the present invention.

FIG. 1 is a perspective view of the Suturing Device 10 in accordance with an embodiment of the present invention. FIG. 2 shows the distal end of a needle 11 which is made of hypodermic tubing shaped in a semi-circular fashion as at 12 and lays in a horizontal aspect with a sharp tip 13 that faces the outside radius of the needle suture material S can be advanced through the needle 11; and a surgeon can grab the suture material with a suitable instrument much easier than if the opening was facing the inside radius of the needle. FIG. 2 also shows the transitional portion 14 of the needle 11 that connects the semi-circular portion 12 with a proximal straight portion 15 of the needle, which lays in the axial center of the semi-circular needle. The transitional portion 14 is shaped in such a way that it avoids any sharp turns to avoid any resistance for the passage of suture material. The proximal portion 15 of the needle extends all the way to the top opening of a turning shaft 16.

FIG. 3 shows a distal bushing 17 through which the proximal portion 15 of the needle passes all the way to the top opening of the turning shaft 16. This bushing 17 is connected with a handle 19 by tubing 20 of a diameter that is suitable to fit in the existing cannulus used in laparoscopic surgery, such as 5, 8, 10, 12 mm outside diameter, etc.

FIG. 4 shows the handle 19 of the instrument which is comprised of a stationary portion 21 and a moving portion 22. The distal end of the stationary portion 21 of the handle 19 has a bushing 23 with a central channel 24 through which the turning shaft 16 passes. The outside circumference of the distal portion 25 of the bushing 23 is suited for the attachment of the tube 20 that connects the distal bushing 17 with the proximal bushing 23, and accordingly with the stationary portion 21 of the handle 19.

At the level of the distal portion of the stationary portion 21 of the handle 19 is an extension 26 by which the moving portion of the handle is connected by a joint 27 with the stationary portion 21 of the handle 19. The joint 27 also contains the returning spring 28 for the moving portion 22 of the handle 19.

The middle portion of the stationary portion 21 of the handle 19 has a space 29 for a spool 30 which is held in by a retractable ball 31 that fits in the center hole on each end of the spool 30.

The very proximal end of the stationary portion 21 of the handle 19 has housing 32 for a gear 33 and the proximal end of the turning shaft 16.

The moving portion of the handle 22 on its proximal end has the gear turner 34 that engages with the gear 33 and turns the gear 33 with the turning shaft 16 and the needle 11 up to 360 degrees.

Figure 6:
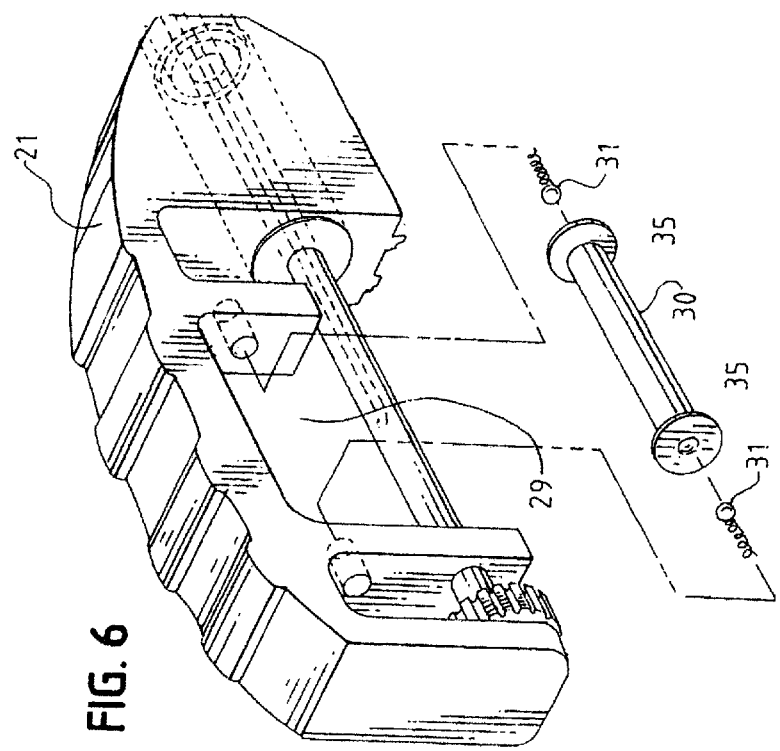
FIG. 6 is an exploded view of the spool housing with the spool of suture material.

FIG. 6 shows the middle portion of the stationary portion 21 of the handle 19 with the space 29 for the spool 30 which is held in by a retractable ball 31 that fits in the center hold 35 on each side of the spool 30.

While the above description and the drawings disclose and illustrate one embodiment of the present invention, one should understand, of course, that the invention is not limited to this embodiment. Those skilled in the art to which the invention pertains may make other modifications and other embodiments employing the principles of this invention, particularly upon considering the foregoing teachings. Therefore, by the appended claims, the applicant

What is claimed is:

1. A suturing apparatus comprising a generally elongate body with a rotatable needle portion having a curved end disposed at a distal end of the body and a handle portion at a proximal end, the handle portion including first and second parts, the first part being moveable with respect to the second part to rotate the needle portion, the handle portion supporting suturing material and the elongate body defining a bore that receives the suturing material and directs it through the body from the proximal end to the distal end and out of the curved end of the needle portion.

2. The apparatus of claim 1, wherein the body includes a tube portion with one end rotatably mounted to the handle portion, the tube portion supporting the needle portion which extends from inside the tube portion and outwardly of it.

3. The apparatus of claim 2, wherein the tube portion lies rotatably mounted to the first part of the handle portion, a pinion secured to the tube portion cooperates with a rack disposed on the second part of the handle portion to translate the relative movement of the first and second parts into rotation of the tube portion.

4. The apparatus of claim 3, wherein the handle portion includes a spool rotatably mounted to the first part of the handle portion for supporting the suture material.

5. The apparatus of claim 1, wherein the curved end of the needle portion has a semi-circular configuration and a sharpened tip cut at an acute angle outwardly and rearwardly from the inner side of the semi-circular part of the middle portion.

6. A suturing apparatus comprising:

a handle with first and second portions secured together for relative movement to one another;

a tube rotatably mounted to the handle and extending outwardly of the handle;

a needle secured to the tube and including a curved end portion;

the handle supporting suture material;

the tube and needle defining bores through which the suture material extends.

7. The apparatus of claim 6, wherein the tube portion lies rotatably mounted to the first part of the handle portion, a pinion secured to the tube portion cooperates with a rack disposed on the second part of the handle portion to translate the relative movement of the first and second parts into rotation of the tube portion.

8. The apparatus of claim 6, wherein the curved end of the needle portion has a semi-circular configuration and a sharpened tip cut at an acute angle outwardly and rearwardly from the inner side of the semi-circular part of the middle portion.

9. The apparatus of claim 7, wherein the handle portion includes a spool rotatably mounted to the first part of the handle portion for supporting the suture material.

* * * * *